US00PP15439P3

(12) United States Plant Patent
Ackerman

(10) Patent No.: US PP15,439 P3
(45) Date of Patent: Dec. 21, 2004

(54) RASPBERRY PLANT NAMED 'PS-1764'

(50) Latin Name: *Rubus idaeus*
Varietal Denomination: PS-1764

(75) Inventor: Stephen M. Ackerman, Salinas, CA (US)

(73) Assignees: Plant Sciences Inc., Watsonville, CA (US); Berry R&D, Watsonville, CA (US)

( * ) Notice: Subject to any disclaimer, the term of this patent is extended or adjusted under 35 U.S.C. 154(b) by 55 days.

(21) Appl. No.: 10/616,833

(22) Filed: Jul. 9, 2003

(65) Prior Publication Data

US 2004/0068775 P1 Apr. 8, 2004

Related U.S. Application Data

(60) Provisional application No. 60/395,103, filed on Jul. 9, 2002.

(51) Int. Cl.[7] ..... A01H 5/00

(52) U.S. Cl. ..... Plt./204

(58) Field of Search ..... Plt./204

*Primary Examiner*—Kent Bell
*Assistant Examiner*—S. B. McCormick-Ewoldt
(74) *Attorney, Agent, or Firm*—Christie, Parker & Hale, LLP

(57) ABSTRACT

This invention relates to a new and distinct everbearing variety of raspberry plant named 'PS-1764'. The new variety is primarily adapted to the growing conditions of the central coast of California and is characterized by the following. Fruit that is very large in size, light in color, glossy with very large druplets. Fall fruit production that begins late with low July–August yields. Primocanes are medium to long in length, large in diameter, medium to light green in color producing very little to no waxy coat and little to no anthocyanins. Thorns are strong and stout in texture with little to no reddish color on the tip.

5 Drawing Sheets

Classification: The variety is botanically known as *Rubus idaeus.*

Varietal denomination: The new raspberry plant has the varietal name of 'PS-1764'.

BACKGROUND OF THE INVENTION

The present invention relates to a new and distinct fall bearing raspberry variety designated as 'PS-1764'. This new variety is a result of a controlled cross between 'PS-127' (U.S. Plant Pat. No. 7,437) and 'Heritage' (unpatented).

The seedling resulting from the aforementioned cross was selected from a controlled breeding plot near Watsonville, Calif. After its selection, the new variety was further asexually propagated in Monterey County and Santa Cruz County, Calif. by dormant canes, roots and non-dormant root shoot cuttings. The new variety was then extensively tested over the next several years in fruiting fields in Monterey County and Santa Cruz County, Calif. This propagation has demonstrated that the combination of traits disclosed herein as characterizing the new variety are fixed and remain true to type through successive generations of asexual reproduction.

BRIEF SUMMARY OF THE INVENTION

'PS-1764' is primarily adapted to the climate and growing conditions of the central coast of California. This region provides the necessary year-round temperatures required for it to produce and maintain a strong vigorous plant with consistent fruit production from July through November on primocanes and in the ensuing year from May through July on the floricanes. The nearby Pacific Ocean provides the needed humidity and moderate temperatures to maintain fruit quality during the production months. The new variety possesses the following traits in combination distinguishing it from other known and closely related commercial varieties in the region. The varieties which we believe to be most closely related to 'PS-1764' are 'PS-1070' (U.S. Plant Pat. No. 11,073), and 'PS-1049' (U.S. Plant Pat. No. 10,142).

COMPARISON TO SIMILAR VARIETIES

In comparison to the similar variety 'PS-1049', 'PS-1764' differs by the following combination of characteristics. 'PS-1764' fall fruit production begins later with lighter July–August production as compared to 'PS-1049'. Floricane fruit production typically is slightly heavier in May yet similar in July as compared to 'PS-1049'. Primocanes are larger in diameter with laterals that are shorter in length as compared to 'PS-1049'. Primocanes of 'PS-1764' also differ by producing very little to no waxy coat on the surface as compared to 'PS-1049' which produces a strong waxy coat. Thorns are slightly shorter in length yet much more abundant along the cane as compared to 'PS-1049'. Thorn tips of 'PS-1764' are very light red-purple in color as compared to 'PS-1049' which tends to be medium red-purple. The foliage of 'PS-1764' is slightly darker green in color and slightly more broad than long as compared to 'PS-1049'. 'PS-1764' has nearly always 3 leaflets per leaf as compared to 'PS-1049' which tends to be nearly equally 3 to 5 leaflets per leaf. Leaf shape of 'PS-1764' tends to be mostly ovate while 'PS-1049' tends to be more cordate in shape. The fruit of 'PS-1764' is larger in size, lighter in color with larger yet fewer druplets per berry as compared to 'PS-1049'. The skin is slightly weaker yet glossler than 'PS-1049'. Seeds are also larger in size as compared to 'PS-1049'.

In comparison to the similar variety 'PS-1070', 'PS-1764' differs by the following combination of characteristics. 'PS-1764' fall fruit production begins much later with lighter July–August production as compared to 'PS-1070'. Floricane fruit production typically is slightly lighter in May yet heavier in July as compared to 'PS-1070'. Primocanes are taller in height, larger in diameter with laterals that are slightly longer in length as compared to 'PS-1070'. Primocanes of 'PS-1764' also differ by producing very little to no waxy coat on the surface with also little to no anthocyanins as compared to 'PS-1070' which produces a medium waxy coat with medium anthocyanins. Thorns are slightly longer in length yet much more abundant along the cane as compared to 'PS-1070'. Thorn tips of 'PS-1764' are very light red-purple in color as compared to 'PS-1070' which tends to be medium red-purple. The foliage of 'PS-1764' is slightly darker green in color, slightly more broad than long with longer petioles as compared to 'PS-1070'. Leaf shape of 'PS-1764' tends to be mostly ovate while 'PS-1070' tends to be more cordate in shape. The fruit of 'PS-1764' is much larger in size, more conical in shape with larger druplets per berry as compared to 'PS-1070'. The skin is slightly weaker yet glossier with better overall appearance than 'PS-1070'. Seeds are also larger in size as compared to 'PS-1070'.

In comparison to the parent variety 'PS-127', 'PS-1764' differs by the following combination of characteristics. 'PS-1764' fall fruit production begins later with a lighter total fall yield. Floricane fruit production also begins later than 'PS-127'. 'PS-1764' fruit size, seed size and druplet size are much larger as compared to 'PS-127'. The foliage of 'PS-1764' is slightly darker green in color and slightly larger in overall size as compared to 'PS-127'. The leaf cross-section of 'PS-1764' is less convex as compared to 'PS-127'.

In comparison to the parent variety 'Heritage', 'PS-1764' differs by the following combination of characteristics. 'PS-1764' fall fruit production begins later with a lighter total fall yield. 'PS-1764' fruit size, seed size and druplet size are much larger as compared to 'Heritage'. The foliage of 'PS-1764' is slightly more broad than long and slightly larger in overall size as compared to 'Heritage'. 'PS-1764' has nearly always 3 leaflets per leaf as compared to 'Heritage' which is mostly 3 to 5 leaflets per leaf.

BRIEF DESCRIPTION OF THE DRAWINGS

The accompanying color photographs show typical specimens of the new variety at various stages of development as nearly true as it is possible to make in color reproductions. The depicted plant and plant parts were approximately 6 to 9 months old.

DETAILED BOTANICAL DESCRIPTION

Figure 1:
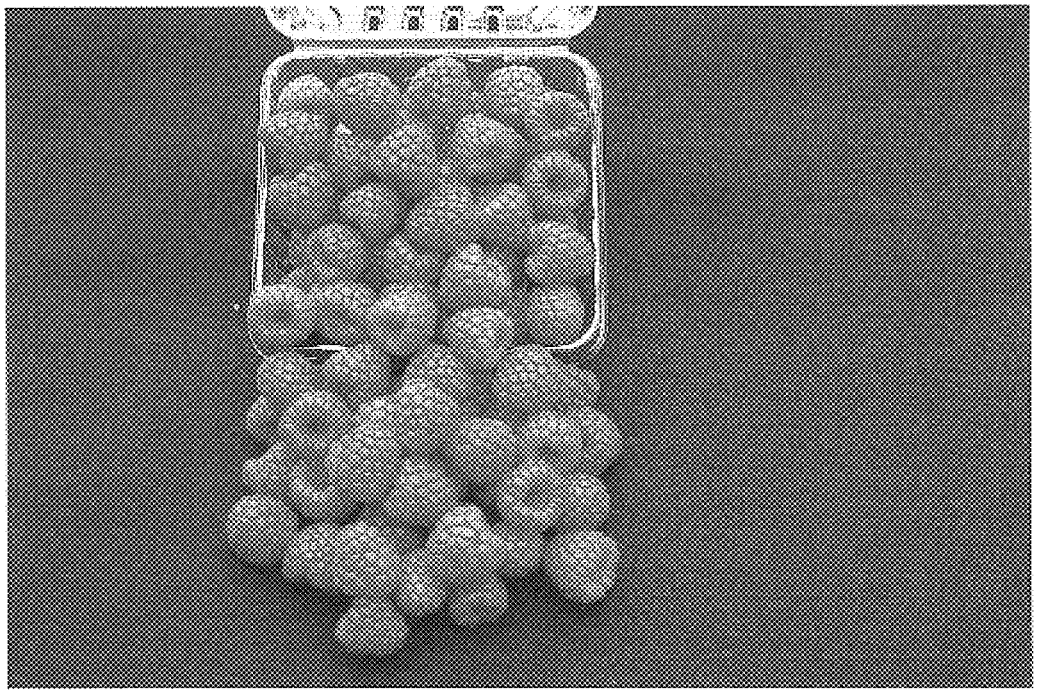
FIG. 1 is a photograph of fruit taken in the month of June.
Figure 2:
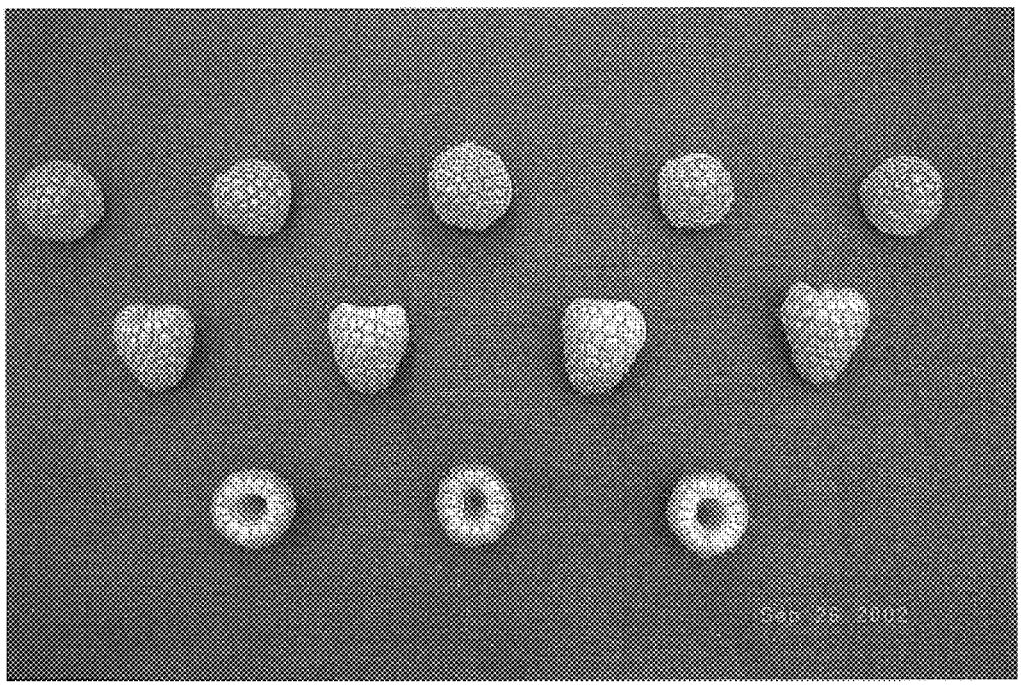
FIG. 2 is a photograph showing typical fruit characteristics taken in the month of September.
Figure 3:
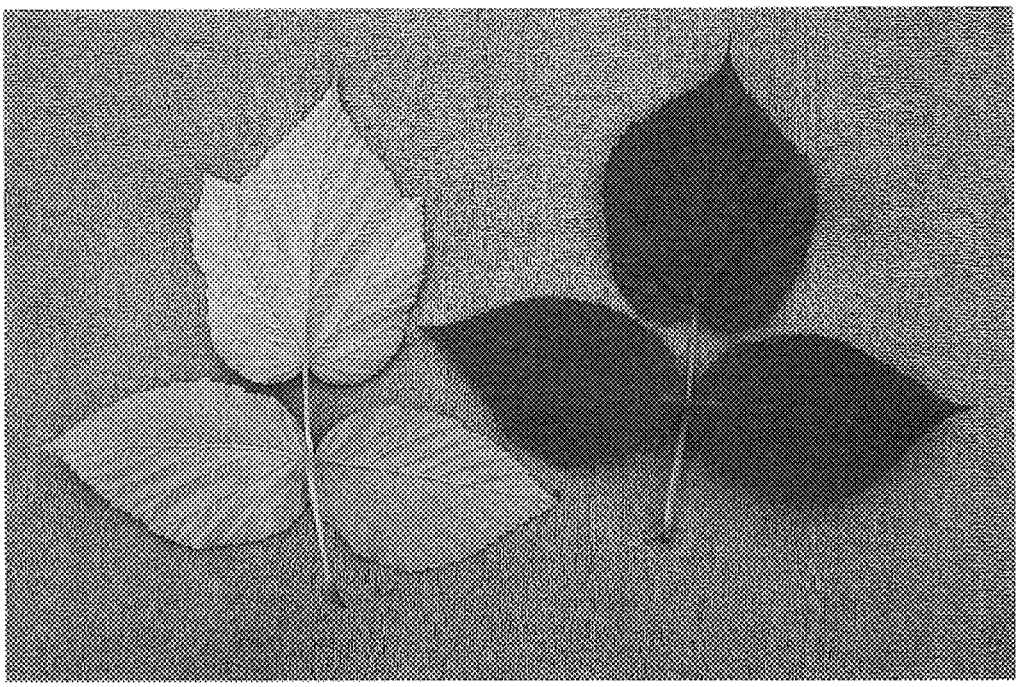
FIG. 3 is a photograph showing typical leaf characteristics taken in the month of August.
Figure 4:
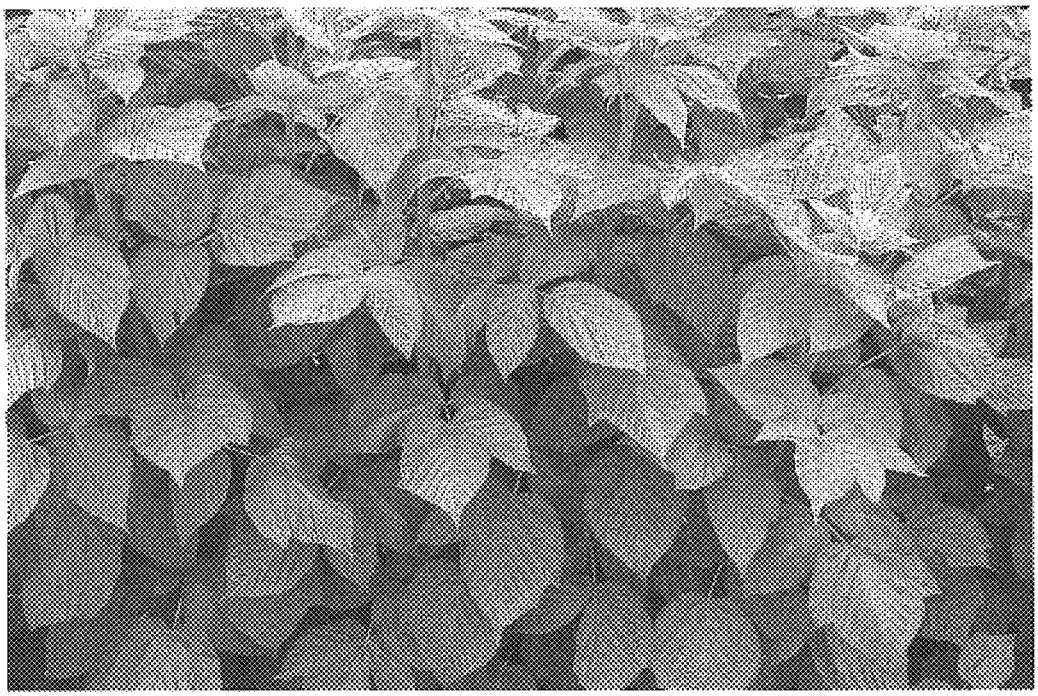
FIG. 4 is a photograph of primocane foliage taken in the month of June.
Figure 5:
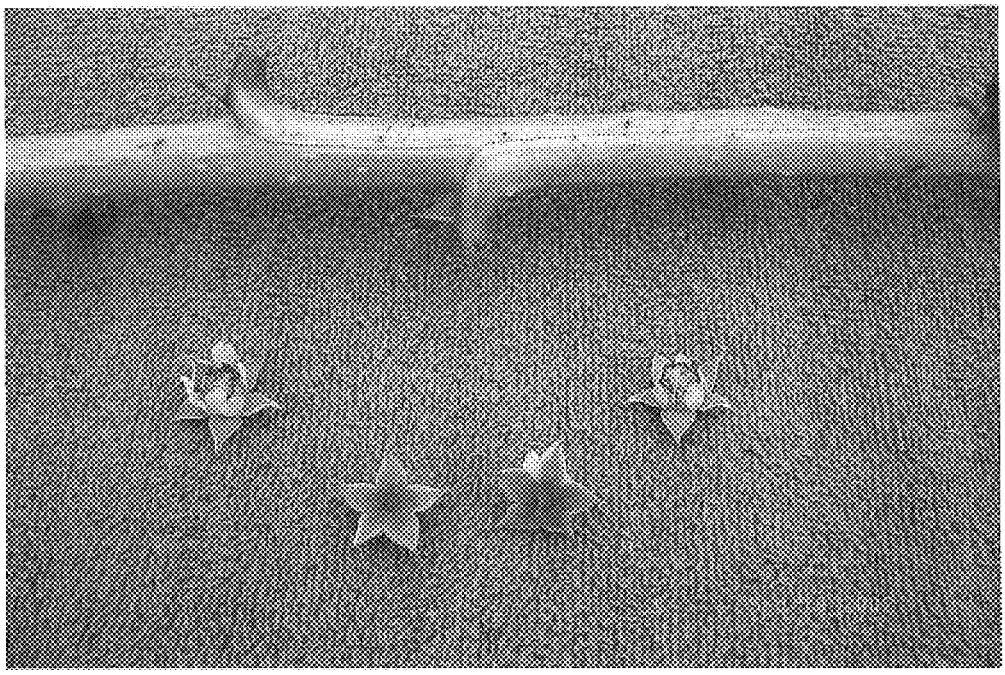
FIG. 5 is a photograph showing typical primocane and flower characteristics taken in the month of September.

The following description of 'PS-1764' unless otherwise noted, is based on observations taken in Watsonville, Calif. These measurements and ratings were taken from plants dug from a nursery located in Monterey County, Calif. during the middle of November and planted approximately 3 to 4 weeks later in Watsonville, Calif. The approximate age of the observed plants were 8 to 9 months old. Yield observations and fruit quality characteristics are averaged from data collected during the 1998 through 2002 production seasons. The phenotypical descriptions, measurements and color designations stated for the new variety may vary, depending upon variations in environmental factors, including weather (temperature, humidity and light intensity), day length, soil type, location and cultural conditions. 'PS-1764' has not been observed under all possible environmental conditions. Color terminology where noted follows the Munsell Book of Colors, Munsell Color, Baltimore, Md. (1976).

FRUIT CHARACTERISTICS

TABLE 1

1998–2002 average market fruit yield and fruit size characteristics of 'PS-1764' with standards from Watsonville, California.

| Character | 'PS-1764' | 'PS-1049' | 'PS-1070' |
|---|---|---|---|
| Primocane Yield July–August mean (gm/pl) | 265 | 512 | 860 |
| Primocane Yield Season Total mean (gm/pl) | 1864 | 1721 | 1510 |
| Floricane Yield May mean (gm/pl) | 117 | 45 | 189 |
| Floricane Yield July mean (gm/pl) | 811 | 856 | 390 |
| Floricane Yield Season Total mean (gm/pl) | 2526 | 1740 | 1613 |
| Primocane Fruit Size mean (gms) | 3.7 | 2.8 | 2.4 |
| Floricane Fruit Size mean (gms) | 3.6 | 2.5 | 2.2 |

Fruit was harvested from July through October (primocanes) and May through July (floncanes).

TABLE 2

Comparison of mature fruit characteristics of 'PS-1764', with standards from Watsonville, California, Sep. 18, 2002

| Character | 'PS-1764' | 'PS-1049' | 'PS-1070' |
|---|---|---|---|
| Munsell Color Range mature fruit | 7.5R 3/12 to 4/12 | 5R 3/6 to 3/8 | 7.5R 4/10 to 3/10 |
| Fruit Length mean (cm) | 2.3 | 2.2 | 1.8 |
| Fruit Width mean (cm)* | 2.1 | 2.0 | 1.8 |
| Fruit Length/ Width Ratio | 1.1 | 1.1 | 1.0 |
| Calyx Diameter mean (cm) | 2.8 | 2.6 | 2.4 |
| Druplets/Berry mean | 68 | 79 | 62 |
| Seed Weight mean (mgs) | 1.6 | 1.3 | 1.4 |

*Width is measured across the widest part of the berry, typically across the shoulders

TABLE 3

Comparison of 1999–2002 primocane fruit quality characteristics of 'PS-1764' with Standards from Watsonville, California.*

| Character | 'PS-1764' | 'PS-1049' | 'PS-1070' |
|---|---|---|---|
| Skin Firmness | 7.8 | 8.7 | 8.3 |
| Fruit Appearance | 8.0 | 8.0 | 7.8 |
| Fruit Gloss | 8.2 | 7.6 | 7.8 |

*Results are averaged from 4 years of replicated fruit quality test performed from August through October 1999–2002.
Ratings are based on a scale from 1–10; the higher the rating, the stronger the skin and more attractive and glossy the berry.

Fruit:

*Size*.—Large to very large.
*Ratio of length/width*.—Slightly longer than broad.
*Predominant shape*.—Conical.
*Color of mature fresh fruit*.—Light red.
*Evenness of color*.—Even.
*Glossiness*.—Strong.
*Adherence of recepticle*.—Very weak.
*Firmness of flesh*.—Firm to very firm.
*Firmness of skin*.—Weak to medium.
*Recepticle size*.—Medium to medium-large.
*Core cavity size*.—Medium large to large.
*Druplet size*.—Medium to large.
*Druplet arrangement around the berry*.—Slightly irregular.
*Primocane time of fruiting*.—Late.
*Floricane time of fruiting*.—Medium.
*Type of bearing*.—Everbearing.

PLANT CHARACTERISTICS

TABLE 4

Comparison of mature cane characteristics of 'PS-1764' compared with standards from Watsonville, California.

| Character | 'PS-1764' | 'PS-1049' | 'PS-1070' |
|---|---|---|---|
| PRIMOCANE August 31, 2002 | | | |
| Munsell Color Range | 5GY 6/6 to 5/6 | 5GY 7/4 to 6/4 | 5GY 6/6 to 7/6 |
| Length mean (m) | 1.8 | 1.9 | 1.4 |
| Lateral Length mean (cm) | 35.9 | 67.8 | 24.1 |
| Basal Diameter mean (mm) | 13.8 | 12.8 | 11.5 |
| Canes/Crown | 2.6 | 2.4 | 3.2 |
| Cane Diameter central ⅓ mean (mm) | 12.6 | 11.4 | 9.0 |
| Fruiting Laterals per cane | 16.8 | 16.3 | 13.6 |
| of cane fruiting | 30.2 | 40.5 | 37.7 |
| Internode length central ⅓ mean (cm) | 3.6 | 5.1 | 4.3 |
| Thorn Length central ⅓ mean (mm) | 2.0 | 2.3 | 1.8 |
| Thorns/cm central ⅓ mean | 9.4 | 3.3 | 4.2 |
| FLORICANE May 30, 2002 | | | |
| Munsell Color Range | 5YR 3/6 to 4/6 | 5YR 4/4 to 4/6 | 5YR 5/4 to 6/4 |
| Length mean (m) | 1.49 | 1.2 | N/A |

Plant:

*Habit*.—Erect to very erect.
*Density*.—Medium dense to dense.
*Size*.—Medium large to large.
*Productivity*.—High.
*Root development*.—Root development initiated in about 1 to 3 months.

Primocanes/floricanes:

*Primocane color*.—Medium to light green yellow.
*Primocane anthocyanin coloration*.—Absent to very weak.
*Primocane thorn density*.—Many.
*Floricane color*.—Medium to dark yellow brown.
*Production of waxy coat*.—Very thin to none.

Young shoots:

*Number*.—Medium.
*Anthocyanin coloration*.—Absent to very weak.
*Thorn density*.—Strong.

Thorns:

*Color (tip)*.—7.5RP 5/4 very light reddish purple.
*Color (base)*.—Light green yellow.
*Texture*.—Rigid.
*Attitude of the tip*.—Horizontal.

FOLIAGE CHARACTERISTICS

TABLE 5

Comparison of mature leaf characteristics of 'PS-1764', compared with standards from Watsonville, California, Aug. 15, 2002

| Character | 'PS-1764' | 'PS-1049' | 'PS-1070' |
|---|---|---|---|
| Munsell Color Range (upper surface) | 7.5GY 2/4 to 3/4 | 7.5GY 3/4 to 4/4 | 5GY 3/4 to 3/6 |
| Munsell Color Range (lower surface) | 5GY 6/2 to 7/2 | 5GY 5/4 to 6/4 | 5GY 5/4 to 6/4 |
| Terminal Leaflet length mean (cm)* | 13.8 | 14.9 | 14.2 |
| Terminal Leaflet width mean (cm)* | 10.9 | 10.2 | 9.7 |
| Terminal Leaflet ratio (L/W) | 1.3 | 1.5 | 1.5 |
| Petiole Length mean (cm) | 7.4 | 7.2 | 5.7 |
| Petiole Width mean (mm) | 3.5 | 3.2 | 3.1 |
| Rachis Length** mean (cm) | 4.6 | 4.5 | 4.1 |
| Thorns/Petiole mean | 16.8 | 18.6 | 12.3 |
| Stipule Length mean (mm) | 9.8 | 10.1 | 8.8 |
| Lateral Leaflet basal pair length mean (cm) | 12.0 | 12.1 | 10.8 |
| Lateral Leaflet basal pair width mean (cm) | 7.2 | 7.2 | 7.0 |

*Terminal leaflets measurements are taken from a 3 leaflet leaf.
**Rachis length = length between the terminal leaflet and the adjacent lateral leaflets of a 3 leaflet leaf Foliage:

*Color of upper surface*.—Medium to medium dark green.
*Color of under side*.—Light to pale grey green.
*Shape in cross section*.—Flat to strongly convex.
*Arrangement*.—Compound.
*Relief between veins*.—Medium to strong.
*Glossiness*.—Medium.
*Number of leaflets/leaf*.—Mostly to always three.

Terminal leaflet:

*Size*.—Medium to large.
*Shape*.—Ovate.
*Length/width ratio*.—Longer than broad.
*Shape of base*.—Cordate.

*Shape of tip*.—Acuminate.
*Margins*.—Biserrate.

Lateral leaflet:
*Size*.—Medium to large.
*Shape*.—Ovate.
*Overlapping*.—Touching to free.
*Orientation*.—Opposite.
*Shape of the base*.—Obtuse.
*Shape of the tip*.—Acuminate.
*Margins*.—Biserrate.
*Rachis length*.—Long.

Petiole:
*Texture*.—Pubescence.
*Thorn orientation*.—Erect.
*Anthocyanin coloration*.—Absent to very weak.
*Stipule orientation*.—Erect.

FLOWERS

TABLE 6

Comparison of mature flower characteristics of 'PS-1764', compared with standards from Watsonville, California, Aug. 23, 2002

| Character | 'PS-1764' | 'PS-1049' | 'PS-1070' |
|---|---|---|---|
| Calyx Diameter mean (cm) | 3.0 | 2.6 | 2.1 |
| Petal Length mean (mm) | 7.5 | 6.9 | 6.6 |
| Petal Width mean (mm) | 4.4 | 3.5 | 2.9 |
| Petal Ratio (L/W) | 1.7 | 2.0 | 2.3 |
| Petals/Flower mean | 5.0 | 5.1 | 5.0 |
| Sepals/Flower mean | 5.3 | 5.0 | 5.1 |

Flowers:
*Color*.—White.
*Size*.—Medium to large, about 3 cm.
*Size of calyx relative to corolla*.—Larger.
*Relative position of petals*.—Free.
*Petal length/width ratio*.—Longer than broad to much longer than broad.

Reproductive organs:
*Pistils*.—Average 60 to 90 per flower and medium to large in size.
*Stamens*.—Average 90 to 130 per flower and medium to large in size.

Hardiness: Winter hardiness and drought/heat tolerances were not observed.

Pest reactions: This new variety may not be resistant to any of the known insects, diseases or viruses common in California. It is known to be moderately susceptible to the two-spotted spider mite. It is also known to be moderately susceptible to powdery mildew and highly susceptible to yellow rust. The susceptibility of the new variety to any of the virus complexes of California has not been determined.

I claim:

1. A new and distinct raspberry plant as herein described and illustrated by the characteristics set forth above.

* * * * *